United States Patent
Battefeld et al.

(10) Patent No.: US 12,287,316 B2
(45) Date of Patent: Apr. 29, 2025

(54) WATER SAMPLING IMMERSION PROBE

(71) Applicant: HACH LANGE GMBH, Berlin (DE)

(72) Inventors: Manfred Battefeld, Dusseldorf (DE);
Frank Steinhauer, Berlin (DE);
Aurelia Stellmach-Hanulok, Wülfrath (DE); Nina Aleth, Krefeld (DE); Silke Brubaker, Mettmann (DE); Axel Leyer, Mönchengladbach (DE);
Hartmut Dräger, Berlin (DE);
Sebastian Goertz, Nettetal (DE);
Michael Kussmann, Düsseldorf (DE);
Michael Küppers, Kaarst (DE)

(73) Assignee: HACH LANGE GMBH, Berlin (DE)

( * ) Notice: Subject to any disclaimer, the term of this patent is extended or adjusted under 35 U.S.C. 154(b) by 356 days.

(21) Appl. No.: 17/632,061

(22) PCT Filed: Aug. 1, 2019

(86) PCT No.: PCT/EP2019/070815
§ 371 (c)(1),
(2) Date: Feb. 1, 2022

(87) PCT Pub. No.: WO2021/018404
PCT Pub. Date: Feb. 4, 2021

(65) Prior Publication Data
US 2022/0268755 A1    Aug. 25, 2022

(51) Int. Cl.
*G01N 33/18* (2006.01)
*B01D 63/06* (2006.01)
(Continued)

(52) U.S. Cl.
CPC ......... *G01N 33/1886* (2013.01); *B01D 63/06* (2013.01); *B01D 63/082* (2013.01);
(Continued)

(58) Field of Classification Search
CPC ................ G01N 33/1886; G01N 1/14; G01N 2001/1043; G01N 33/1813; G01N 1/12;
(Continued)

(56) References Cited

U.S. PATENT DOCUMENTS 4,960,510 A * 10/1990 Wolff ................... B01D 29/445
   209/405
6,811,842 B1 * 11/2004 Ehrnsperger ......... B01D 61/005
   604/385.101
(Continued)

FOREIGN PATENT DOCUMENTS

CN    102390893 A       3/2012
CN    202638673 U *     1/2013
(Continued)

OTHER PUBLICATIONS

CN-202638673-U (Year: 2013).*
(Continued)

*Primary Examiner* — Kristina M Deherrera
*Assistant Examiner* — Fatemeh Esfandiari Nia
(74) *Attorney, Agent, or Firm* — Ference & Associates LLC

(57) ABSTRACT

The present invention relates to a water sampling immersion probe (50) for continuously filtering a water sample from wastewater (14). The water sampling immersion probe (50) includes a distal coarse filter (60) with a porosity of 0.1 to 1.0 mm, a proximal fine filter (70) arranged downstream of the coarse filter (60) and having a porosity of less than 5.0 μm, and a sample suction opening (74) arranged downstream of the fine filter (70). The coarse filter (60) is arranged to not contact the fine filter (70).

15 Claims, 3 Drawing Sheets

(51) Int. Cl.
*B01D 63/08* (2006.01)
*B01D 69/02* (2006.01)
*B01D 69/04* (2006.01)
*B01D 69/06* (2006.01)
*C02F 1/44* (2023.01)
*G01N 1/10* (2006.01)
*G01N 1/14* (2006.01)

(52) U.S. Cl.
CPC ............ *B01D 69/02* (2013.01); *B01D 69/04* (2013.01); *B01D 69/06* (2013.01); *C02F 1/44* (2013.01); *G01N 1/14* (2013.01); *B01D 2313/16* (2013.01); *B01D 2313/23* (2013.01); *B01D 2313/243* (2013.01); *B01D 2319/02* (2013.01); *B01D 2325/02* (2013.01); *G01N 2001/1043* (2013.01)

(58) Field of Classification Search
CPC .... G01N 33/182; B01D 63/06; B01D 63/082; B01D 69/02; B01D 69/04; B01D 69/06; B01D 2313/16; B01D 2313/23; B01D 2313/243; B01D 2319/02; B01D 2325/02; B01D 29/01; B01D 29/114; B01D 29/58; B01D 35/02; B01D 2201/087; C02F 1/44

See application file for complete search history.

(56) References Cited

U.S. PATENT DOCUMENTS

| | | | |
|---|---|---|---|
| 2002/0185430 A1 | 12/2002 | Choi | |
| 2004/0161935 A1* | 8/2004 | Tsuihiji | B01D 69/14 438/689 |
| 2009/0324929 A1* | 12/2009 | Yamakawa | B01D 67/0013 156/60 |
| 2014/0042078 A1* | 2/2014 | Hwang | B01D 29/03 210/413 |
| 2018/0052080 A1 | 2/2018 | Thomas et al. | |
| 2021/0148797 A1* | 5/2021 | Packingham | G01N 1/40 |

FOREIGN PATENT DOCUMENTS

| | | | |
|---|---|---|---|
| CN | 208140415 U | 11/2018 | |
| CN | 208505675 U | 2/2019 | |
| CN | 208689047 U | 4/2019 | |
| DE | 102004037226 B3 * | 8/2005 | .......... B01D 29/114 |
| DE | 102018113619 A1 | 12/2019 | |

OTHER PUBLICATIONS

DE-102004037226-B3 (Year: 2005).*
European Patent Office, International Search Report, May 13, 2020, 4 pages.

* cited by examiner

WATER SAMPLING IMMERSION PROBE

The present application is a National Phase Entry of PCT International Application No. PCT/EP2019/070815, which was filed on Aug. 1, 2019, the contents of which are hereby incorporated by reference.

The present invention relates to a water sampling immersion probe for continuously filtering a water sample from wastewater.

Stationary water sampling immersion probes are used as a part of a process water analysis arrangement for analyzing one or more analytes in water, for example, in wastewater in a wastewater tank being a part of a wastewater treatment plant.

A typical stationary water sampling immersion probe is described in DE 10 2004 037 226 B3. This water sampling immersion probe is provided with two single inclined filter membranes which are cleaned intermittently by providing air bubbles at the membrane bottom. The air bubbles rise along the surface of the filter membranes and thereby mechanically clean the surface of the filter membranes. However, some substances of wastewater, such as oil and grease, adhere at the distal surface of the filter membranes and cannot be removed from the membrane filter surface by the rising air bubbles so that the membrane filter eventually becomes clogged.

An object of the present invention is to provide an improved water sampling immersion probe which is more robust against clogging.

This object is solved with a water sampling immersion probe with the features of claim 1.

The water sampling immersion probe for continuously filtering a water sample from wastewater comprises at least a pair of cooperating filters, the filter pair comprising a distal coarse filter with a porosity of 0.1 to 1.0 mm, and a proximal fine filter downstream of the coarse filter. The fine filter has a porosity of less than 5.0 µm. The coarse filter and the fine filter do not contact or touch each other, but are arranged at a distance from each other.

The distance between the two filter membranes of the pair of filters avoids having substances, which are withheld by the coarse filter or which adhere to the outside of the coarse filter, from directly contacting the fine filter. Oil and grease which are withheld by the distal coarse filter therefore do not contact the proximal fine filter so that the fine filter is reliably protected and does not become clogged. The fine filter is provided for filtering only relatively fine particles of the wastewater so that a mechanical damage of the fine filter is reliably avoided.

A sample suction opening is provided downstream of the fine filter so that a filtered water sample can be sucked through the sample suction opening and can be pumped to a water analysis apparatus which is arranged remote from the water sampling immersion probe, for example, arranged in a central control station of the wastewater treatment plant.

The water sampling immersion probe is arranged so that it is continuously immersed into water and is preferably not provided with any measurement equipment.

The term "distal" in this context means: orientated to the outside of the immersion probe and directed to the wastewater. The term "proximal" in this context means: orientated to the suction side of the immersion probe.

The water sampling immersion probe is typically used in the primary tank of a wastewater treatment plant so that the wastewater potentially comprises relatively large particles and elements, for example, oil, grease etc. The immersion probe is used to extract a water sample free of particular elements which is pumped to a water analysis apparatus which analyzes, for example, the quantity of phosphate and/or ammonium.

According to a preferred embodiment of the present invention, the space between the coarse filter and the fine filter defines a venting chamber which is provided with at least one venting opening through which venting air can be blown into the venting chamber. The venting chamber is mechanically closed so that the air which is blown into the venting chamber through the venting opening can leave the venting chamber only via the fine pores of the coarse filter. The venting of the venting chamber generates air bubbles which rise up along the distal surface of the fine filter. The rising air bubbles generates a localized turbulence at the fine filter surface so that small particles adhering to the distal coarse filter surface are carried away from the filter surface, thereby mechanically cleaning the fine filter.

The air blown into the venting chamber can only leave the venting chamber through the coarse filter from its proximal side to its distal side so that the coarse filter is mechanically cleaned by the air streaming through the pores of the coarse filter. The air streaming through the pores of the coarse filter removes and/or takes away the adhering particles, such as oil and/or grease, from the coarse filter surface back into the wastewater.

According to a preferred embodiment of the present invention, the fine filter is defined by an air-impermeable fine filter membrane. Since the fine filter membrane is not permeable to air, a relatively high air pressure can be generated within the venting chamber to thereby generate a relatively high fluidic flow speed through the coarse filter pores so that, at the distal side of the coarse filter pores, a strong turbulence is generated that provides a strong mechanical cleaning performance at the coarse filter membrane.

According to a preferred embodiment of the present invention, the coarse filter is defined by a self-supporting coarse filter membrane. The coarse filter membrane does not need to be mechanically supported by a separate structure.

According to a preferred embodiment of the present invention, the coarse filter is defined by a coarse filter membrane having a lipophilic surface. Oil and grease adhere at the lipophilic surface of the coarse filter membrane so that oil and grease do not pass the coarse filter membrane in a proximal direction. No oil and grease can therefore contact the fine filter membrane which is sensible for oil and grease.

According to a preferred embodiment of the present invention, a suction chamber is defined and provided downstream of the fine filter. The sample suction opening defines the outlet of the suction chamber. Since the fine filter is relatively thin and mechanically sensible, the fine filter is preferably mechanically supported by a separate stiff support body which is permeable to water. The complete suction chamber is preferably filled with the stiff support body. The stiff support body is in contact with the fine filter membrane and thereby supports the fine filter membrane over its entire surface. Since the water sample is sucked into the suction chamber through the fine filter membrane, the pressure in the suction chamber is lower than at the distal side of the fine filter membrane so that the fine filter membrane is pushed against and is thereby mechanically supported by the stiff support body. Since the support body is permeable to water, the water sample can flow without any substantial flow resistance from the fine filter membrane through the support body to the sample suction opening of the immersion probe.

According to a preferred embodiment of the present invention, the coarse filter membrane of the coarse filter is substantially flat and plane. The coarse filter membrane of the coarse filter and the parallel fine filter membrane of the fine filter are preferably both flat and arranged substantially parallel to each other. The general plane of the coarse filter membrane, of the fine filter membrane, and of the resulting venting chamber are more preferably inclined with respect to the vertical with an inclination angle of 5° to 80°, for example, with an inclination angle of 10° to 40°. The spatial orientation of the filter inclination is provided so that the coarse filter membrane is orientated downwards and the fine filter membrane is orientated upwards. The venting chamber between the filter membranes is vented at the bottom of the venting chamber so that the rising air bubbles remain in contact with the distal side of the fine filter membrane over the entire height of the fine filter membrane.

In an alternative embodiment of the present invention, the coarse filter membrane and the fine filter membrane are generally cylindrical in shape and are arranged coaxially with each other. The general shape of the sampling immersion probe is preferably cylindrical. The generally cylindrical shape of the immersion probe provides a "shape redundancy" because, even if a sector of the cylindrical filter membranes is intensively exposed to a wastewater current and is thereby exposed to a high load of particles and substances adhering to the filter membranes, there will always be another sector at the lee side of the cylindrical immersion probe which is less exposed to particles and substances of the wastewater current. The venting chamber is preferably also generally cylindrical, the venting opening being provided at the vertically lowest region of the venting chamber. If the cylindrical venting chamber is orientated vertically, so that the longitudinal axis of the cylinder is orientated vertically, the venting opening is provided at the bottom circular ring wall axially delimiting the cylindrical venting chamber. Numerous venting openings are preferably provided.

The cylinder axis of the generally cylindrical immersion probe is more preferably inclined with respect to the horizontal with an inclination angle of 10° to 80°. The spatial orientation of the filter inclination is realized so that the axial end comprising the venting opening is located lower than the axial end which is not provided with a venting opening.

According to a second aspect of the present invention, the immersion probe is provided with a protection fork with at least two fork tines, i.e., fork teeth or fork prongs. The protection fork is provided at the outside of the coarse filter membrane but does not necessarily directly contact the coarse filter membrane. The lateral distance of two neighboring fork tines to each other is preferably between 5 mm and 50 mm. The protection fork provides a wide-meshed outside shielding of the coarse filter membrane against large waste/garbage pieces such as sheets, layers and foils of a flexible nature which could otherwise cover a large area of the distal surface of the coarse filter membrane.

The protection fork is generally an independent invention which could be used with any kind of water sampling immersion probe, even with water sampling immersion probes with only one single filter membrane.

The distance of the fork tines to the coarse filter is preferably in the range of a few millimeters to a few centimeters so that a continuous exchange of the wastewater layer adjacent to the coarse filter membrane is provided. The fork tines provide that relatively large waste/garbage pieces cannot directly cover the distal surface of the coarse filter membrane.

According to a preferred embodiment of the present invention, the free ends of the fork tines are provided downstream in a flowing wastewater environment, and/or are provided higher than the closed ends of the fork tines. The free ends of the fork tines are generally orientated and arranged at the lee side in the wastewater current so that no garbage pieces can be spiked by the free ends of the fork tines.

According to a preferred embodiment of the present invention, the distance between the closed fork tine ends and the next upstream flow resistance structure is at least 50 mm. The term "upstream" in this context refers to the direction of the wastewater flow or current with respect to the static immersion probe.

The next upstream flow resistance structure can, for example, be a bow of a holding structure holding the immersion probe in place within the wastewater tank. The minimum distance between the next upstream flow resistance structure and the closed fork tine ends provides that relatively large and flexible wastewater garbage pieces which are stuck at the flow resistance structure cannot interfere with and cannot close the open interspaces between the fork tines.

All the described features of the protection fork are subject the of an independent invention.

According to a general concept of the present invention, a process water analysis arrangement for continuously analyzing water samples of wastewater is provided. The analysis arrangement comprises the water sampling immersion probe as claimed in one of the immersion probe claims. The analysis arrangement also comprises an control unit with a water analysis apparatus. The water analysis apparatus is fluidically connected to the suction opening of the water sampling immersion probe so that the water sample is pumped from the immersion probe by a sample pump to the water analysis apparatus where the water sample is analyzed.

Two embodiments of the present invention are described below with reference to the drawings, wherein:

FIG. 1 schematically shows a process water analysis arrangement including a first embodiment of a generally flat and plane water sampling immersion probe provided in a wastewater tank and including an control unit with a water analysis apparatus which is arranged remote from the immersion probe;

Figure 1:
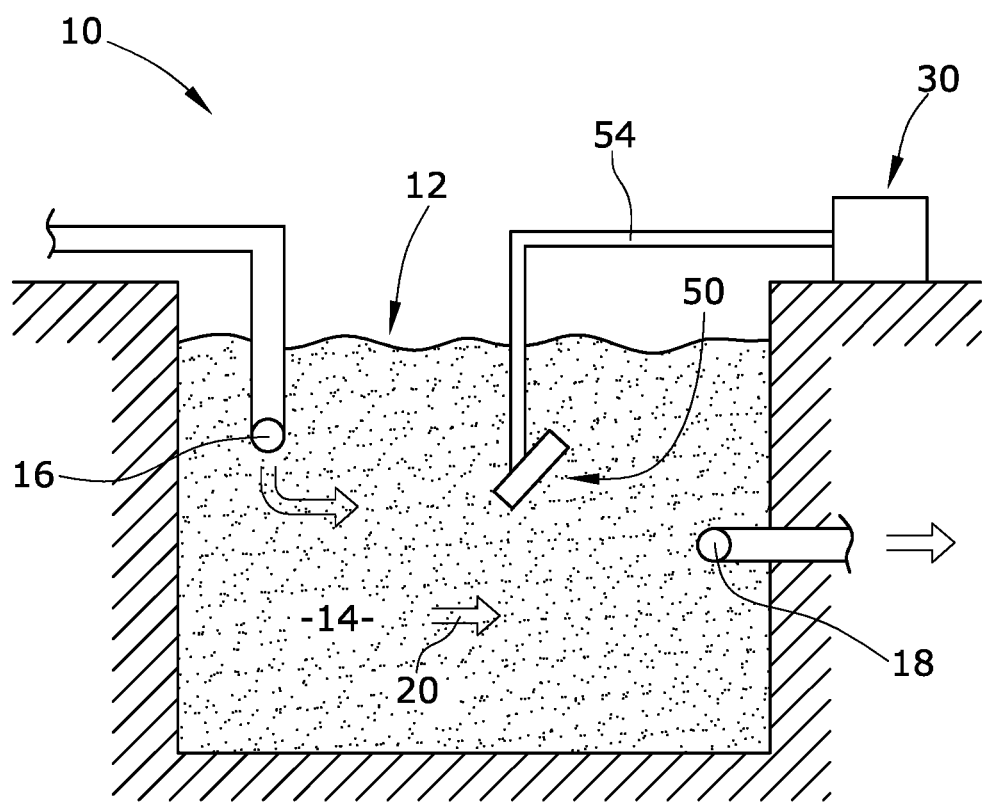

FIG. 1 schematically shows a process water analysis arrangement 10 for continuously analyzing water samples of wastewater 14. The wastewater 14 continuously flows into a primary wastewater tank 12 through a tank inlet 16, and continuously flows out of the wastewater tank 12 through a tank outlet 18, so that a general wastewater flow 20 is generated within the wastewater tank 12 between the inlet 16 and the outlet 18. The process water analysis arrangement 10 is provided for quasi-continuously determining one or more analytes of the wastewater 14, for example, ammonium and/or phosphate and can be a part of a wastewater treatment plant.

The process water analysis arrangement 10 basically comprises a water sampling immersion probe 50 which is immersed into the wastewater 14 and which is held and positioned by a stiff holding structure 54. The immersion probe 50 is fluidically and electronically connected to a land-sided control unit 30 comprising a sample pump 34, a venting air pump 32 and a water analysis apparatus 36 for analyzing one or more analyte of a water sample of the wastewater 14. The analysis apparatus 36 can alternatively be provided remote from the control unit 30 in a control center of the wastewater treatment plant, whereas the control unit 30 with the pumps 32, 34 is located as close as possible to the immersion probe 50.

Figure 2:
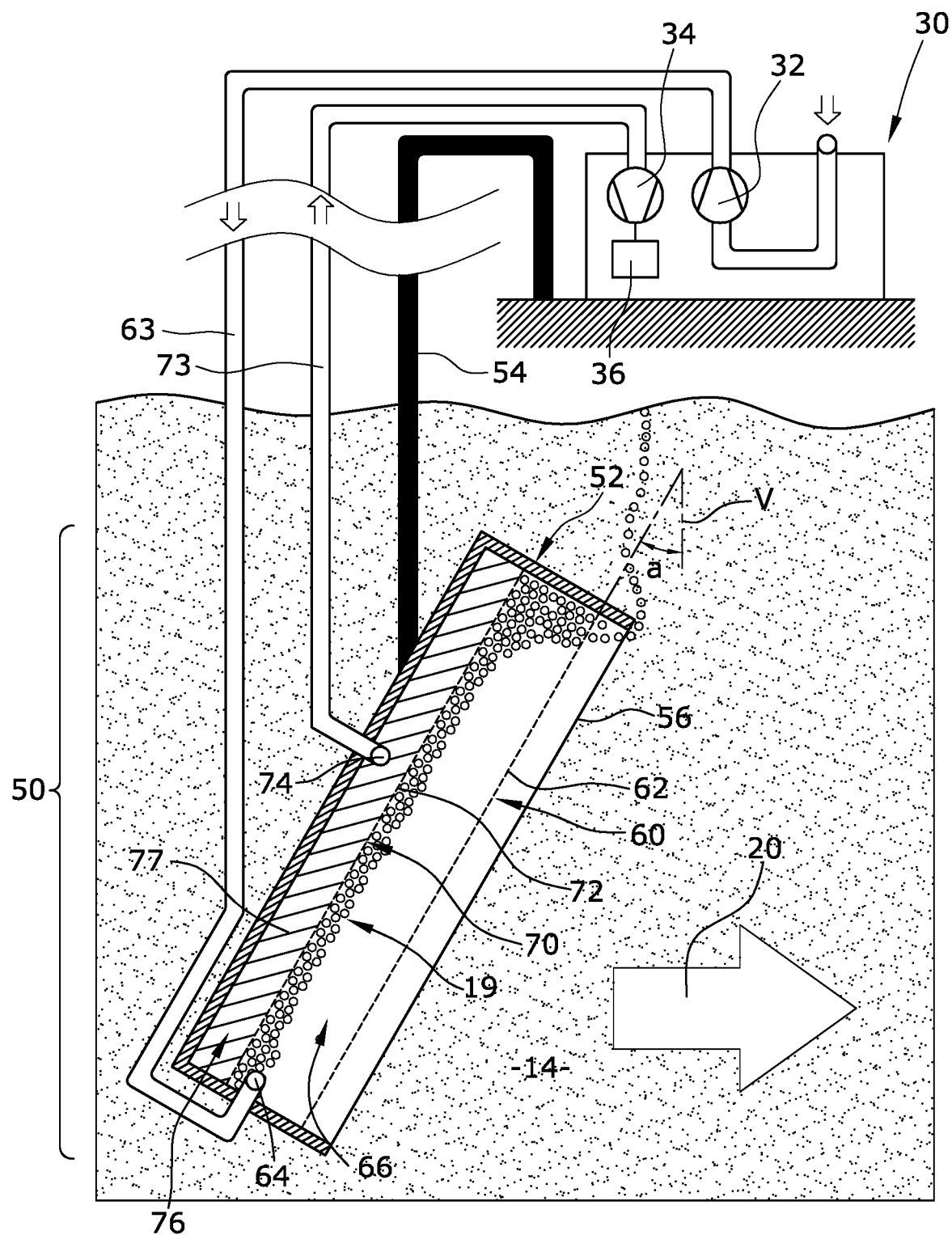
FIG. 2 shows the process water analysis arrangement of FIG. 1 in greater detail.

FIG. 2 shows a first embodiment of a water sampling immersion probe 50 in greater detail. The immersion probe 50 is generally provided as a flat, plane and rectangular body which is defined by a probe housing 52 defining a generally plane and rectangular probe opening 56 at the distal side of the probe housing 52. The probe opening 56 is closed by a distal coarse filter 60 which is defined by a coarse filter membrane 62 with a porosity of about 0.6 mm. The coarse filter membrane 62 is made of stainless steel, is stiff and self-supporting, and has a lipophilic surface.

A fine filter 70 is provided proximal of the coarse filter 60. The fine filter 70 is defined by a plastic fine filter membrane 72 which is substantially air-impermeable and which has a nominal porosity of 50 μm.

The fine filter membrane 72 and the coarse filter membrane 62 do not contact or touch each other, but are provided with a constant distance of a few millimeters to each other over the entire plane surface of the filters 60, 70. The space between the coarse filter 60 and the fine filter 70 defines a plane and rectangular venting chamber 66 which is not filled with any solid substance. The rectangular and generally plane space proximal of the fine filter membrane 72 defines a suction chamber 76 which is completely filled with a separate stiff support body 77 which mechanically supports the fine filter membrane 72. The support body 77 is a stiff plastic body which is permeable to water and air.

The coarse filter membrane 62 and the fine filter membrane 72 are arranged substantially parallel to each other. The general planes of the coarse filter membrane 62 and the fine filter membrane 72 are inclined with respect to the vertical V with an inclination angle a of about 15°.

Numerous venting openings 64 are provided at the bottom of the venting chamber 66 through which venting air bubbles 19 enter the venting chamber 66 and rise upwards along the distal surface of the fine filter membrane 72. The venting openings 64 are provided with venting air via a venting tube 63 which fluidically connects the venting openings 64 with the venting air pump 32 provided at the control unit 30. The air bubbles 19 finally exit the venting chamber 66 through the small pores of the coarse filter membrane 62, and thereby mechanically clean the coarse filter membrane 62 from substances adhering to the distal side of the coarse filter membrane 62.

The sample pump 34 can, alternatively, be provided at the immersion probe 50.

The suction chamber 76 proximal of the fine filter membrane 72 is provided with a sample suction opening 74 through which the filtered water sample is sucked out of the suction chamber 76 and pumped by a sample pump 34 provided at the control unit 30 to the water analysis apparatus 36 of the control unit 30 via a sample line 73.

The process water analysis arrangement 10 generally works intermittently so that a sample suction and analyzing interval is followed by a venting interval which is followed by a sample suction and analyzing interval etc.

An almost continuous sample flow and analysis can be realized by two immersion probes which are working in an alternating manner.

Figure 3:
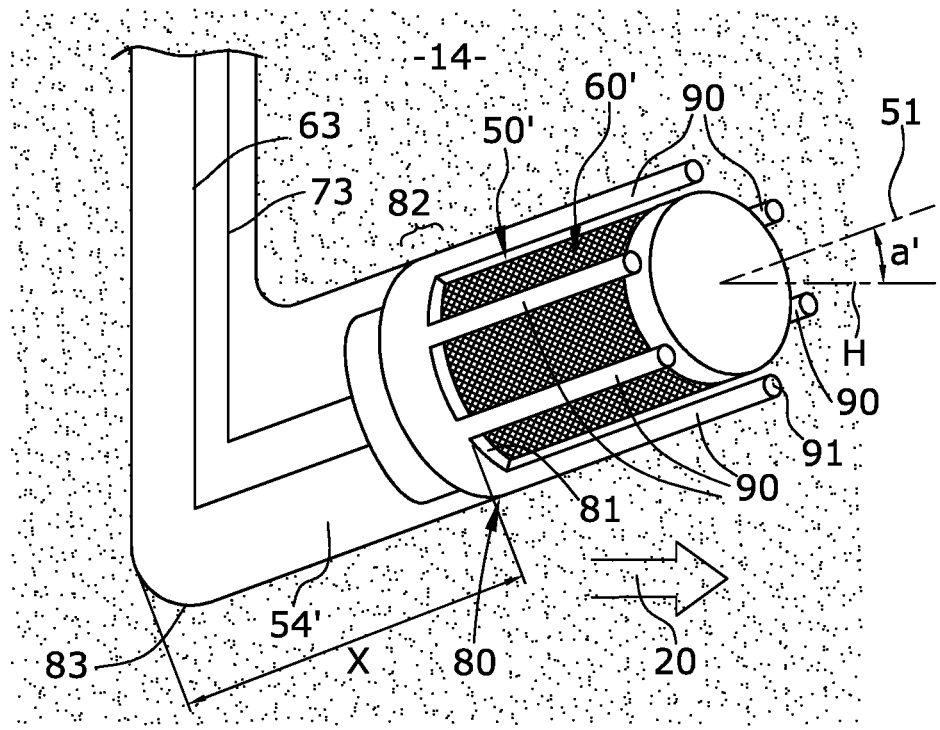
FIG. 3 shows a second embodiment of a water sampling immersion probe with a generally cylindrical shape.
Figure 4:
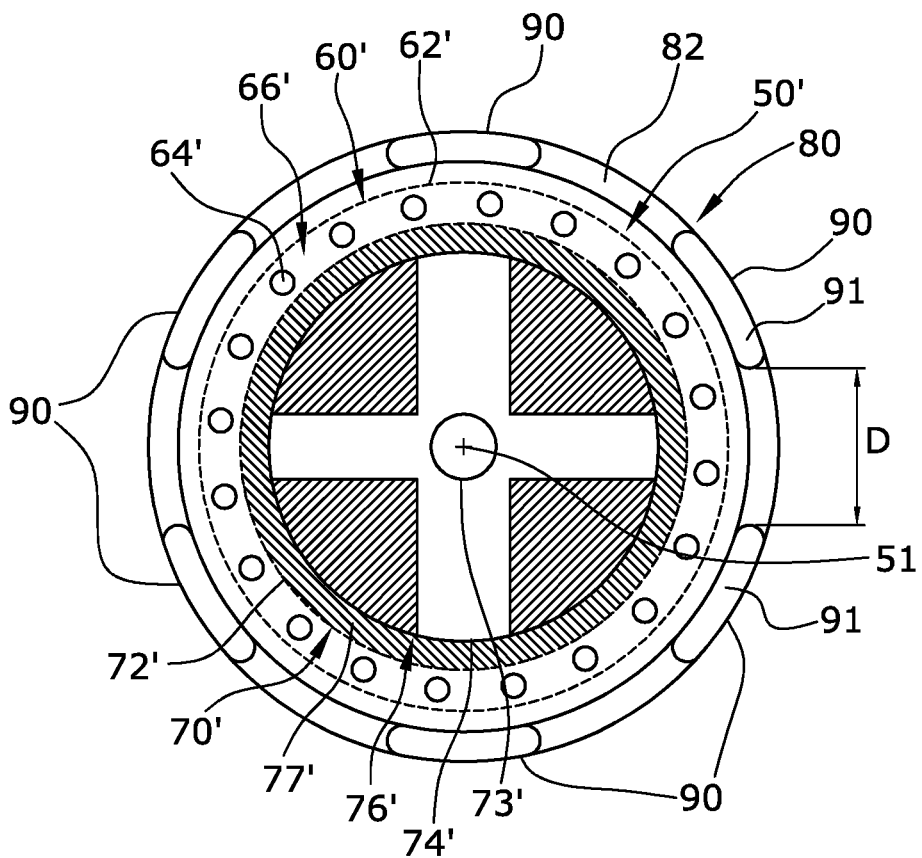
FIG. 4 shows a cross-section of the water sampling immersion probe of FIG. 3.

FIGS. 3 and 4 show a second embodiment of a water sampling immersion probe 50' which is not designed to be generally flat, but which is designed to have a generally cylindrically shape. The reference signs in FIGS. 3 and 4 are generally provided with an apostrophe if the corresponding parts and features are designed differently, but have the same function as at the immersion probe 50 of the first embodiment shown in FIG. 2.

As can be seen best in FIG. 4, the generally cylindrical concept of the immersion probe 50' results in a generally cylindrical coarse filter 60' with a cylindrical coarse filter membrane 62, a generally cylindrical fine filter 70' with a cylindrical fine filter membrane 72', a generally cylindrical and ring-like venting chamber 66', and a generally cylindrical suction chamber 76' with the generally cylindrical support body 77'.

The immersion probe 50' is provided with numerous venting openings 64' at the ring-like cylinder bottom wall of the venting chamber 66'. Four sample suction openings 74' are provided at the proximal suction chamber surface from where the water sample flows to the sample line 73.

As can be seen in FIG. 3, the cylinder axis 51 of the generally cylindrical immersion probe 50' is inclined with respect to the horizontal H in an inclination angle a' of about 20°.

The immersion probe 50' is provided with a generally cylindrical protection fork 80 with six fork tines 90 surrounding the immersion probe 50, and in particular surrounding the coarse filter membrane 72'. The fork tines 90 are generally provided parallel to each other, and the cylinder defined by the fork tines 90 is provided coaxially with the cylindrical immersion probe 50'. The fork tines 90 have a substantially constant cross-section over their entire length.

The orientation of the immersion probe 50' including the protection fork 80 is chosen so that the free ends 91 of the fork tines 90 are at the lee side with respect to the wastewater flow 20 in the wastewater tank 12. The lateral distance D of the fork tines 90 to each other is about 20 mm. The closed ends 81 of the fork tines 90 are provided with a distance X of about 50 mm from the next upstream flow resistance structure 83. The flow resistance structure 83 in this case is a bow shoulder of the probe holding structure 54' which is, in this embodiment, generally cylindrical in cross section and has the same diameter as a cylindrical fork basis 82 of the protection fork 80.

The invention claimed is:

1. A water sampling immersion probe for continuously filtering a water sample from wastewater, the water sampling immersion probe comprising:
   a distal coarse filter comprising a porosity of 0.1 to 1.0 mm;
   a proximal fine filter arranged downstream of the distal coarse filter, the proximal fine filter comprising a porosity of less than 50 μm, the distal coarse filter and the proximal fine filter being arranged so as to not contact each other, wherein the distal coarse filter and the proximal fine filter define a venting chamber, wherein the venting chamber is vented at a bottom and the venting chamber is inclined with respect to vertical with an inclination angle between 5° and 80° degrees and completely submerged so that rising air bubbles remain in contact with a distal side of a membrane of the proximal fine filter over the entire height of the membrane; and
   a sample suction opening arranged downstream of the proximal fine filter.

2. The water sampling immersion probe of claim 1, wherein the venting chamber comprises at least one venting opening through which venting air can be blown into the venting chamber.

3. The water sampling immersion probe of claim 2, wherein,
the water sampling immersion probe is generally cylindrical and comprises a cylinder axis, and
the cylinder axis of the immersion probe is inclined with respect to a horizontal (H) at an inclination angle (A') of 10° to 80°.

4. The water sampling immersion probe of claim 1, wherein the proximal fine filter is defined by a fine filter membrane which is air-impermeable comprising a porosity of less than 5.0 μm.

5. The water sampling immersion probe of claim 1, wherein the distal coarse filter is defined by a coarse filter membrane which is self-supporting.

6. The water sampling immersion probe of claim 5, wherein the coarse filter membrane of the distal coarse filter is substantially flat.

7. The water sampling immersion probe of claim 6, wherein,
the coarse filter membrane of the coarse filter and the fine filter membrane of the fine filter are each flat and are arranged substantially parallel to each other, and
a general plane of each of the coarse filter membrane, the fine filter membrane, and the resulting venting chamber are inclined with respect to the vertical (V) at an inclination angle of 10° to 40°.

8. The water sampling immersion probe of claim 5, wherein the proximal fine filter is defined by a fine filter membrane, wherein the coarse filter membrane and the fine filter membrane are each generally cylindrical in shape and are arranged coaxially with respect to each other.

9. The water sampling immersion probe of claim 8, wherein,
the venting chamber is generally cylindrical, and
the venting opening is arranged at a vertically lowest region of the venting chamber.

10. The water sampling immersion probe of claim 1, wherein the distal coarse filter is defined by a coarse filter membrane which is at least one of self-supporting and comprises a lipophilic surface.

11. The water sampling immersion probe of claim 1, further comprising:
a suction chamber arranged downstream of the proximal fine filter; and
a separate stiff support body arranged in the suction chamber which mechanically supports the proximal fine filter and which is permeable to water.

12. The water sampling immersion probe of claim 1, further comprising:
a protection fork comprising at least two fork tines, the protection fork being arranged distal of and at the outside of the coarse filter membrane, wherein,
a lateral tine distance (D) of two neighboring fork tines of the at least two fork tines is 5 to 50 mm.

13. The water sampling immersion probe of claim 12, wherein,
each of the at least two fork tines comprise a free end and at least one closed end, and
the free end of each of the at least two fork tines are arranged downstream in a direction of a flowing wastewater, and
the free end of each of the at least two fork tines is arranged higher than the at least one closed end of the at least two fork tines in the direction of the flowing wastewater.

14. The water sampling immersion probe of claim 13, further comprising:
a next upstream flow resistance structure, wherein,
a distance (X) between the at least one closed end of the at least two fork tines and the next upstream flow resistance structure is at least 50 mm.

15. A process water analysis arrangement for continuously analyzing a water sample of wastewater, the process water analysis arrangement comprising:
a water sampling immersion probe for continuously filtering a water sample from wastewater, the water sampling immersion probe comprising:
a distal coarse filter comprising a porosity of 0.1 to 1.0 mm;
a proximal fine filter arranged downstream of the distal coarse filter, the proximal fine filter comprising a porosity of less than 50 μm, the distal coarse filter and the proximal fine filter being arranged so as to not contact each other, wherein the distal coarse filter and the proximal fine filter define a venting chamber, wherein the venting chamber is vented at a bottom and the venting chamber is inclined with respect to vertical with an inclination angle between 5° and 80° degrees and completely submerged so that rising air bubbles remain in contact with a distal side of a membrane of the proximal fine filter over the entire height of the membrane; and
a sample suction opening arranged downstream of the proximal fine filter;
a control unit comprising a sample pump, and
a water analysis apparatus,
wherein, the water analysis apparatus is fluidically connected to the sample suction opening so that the water sample is pumped from the water sampling immersion probe by the sample pump to the water analysis apparatus.

\* \* \* \* \*